United States Patent
Clay et al.

[11] Patent Number: 5,871,014
[45] Date of Patent: Feb. 16, 1999

[54] SURGICAL SHOULDER DRAPE

[75] Inventors: Yolanda D. Clay, Douglasville, Ga.; Lee Ann Totten, Chicago, Ill.

[73] Assignee: Allegiance Corporation, McGaw Park, Ill.

[21] Appl. No.: 822,081

[22] Filed: Mar. 20, 1997

[51] Int. Cl.⁶ .................................................. A61B 19/00
[52] U.S. Cl. .......................................... 128/849; 128/853
[58] Field of Search ................................... 128/849–856

[56] References Cited

U.S. PATENT DOCUMENTS

| | | | |
|---|---|---|---|
| 4,041,942 | 8/1977 | Dougan | 128/853 |
| 4,569,341 | 2/1986 | Morris | 128/853 |
| 4,890,628 | 1/1990 | Jackson | 128/853 |
| 5,002,069 | 3/1991 | Thompson | 128/853 |
| 5,515,868 | 5/1996 | Mills | 128/853 |
| 5,618,278 | 4/1997 | Rothrum | 128/853 |

*Primary Examiner*—Michael A. Brown
*Attorney, Agent, or Firm*—Hill & Simpson

[57] ABSTRACT

The present invention pertains to a surgical drape for use during a medical procedure on a shoulder of a patient when the patient is in the so called "beach chair" or Fowlers position. The surgical drape is a one-piece design and has a base panel defining a fenestration which is sealable around the patient's shoulder. Opposing right and left panels extend from the base panel away from the fenestration and a slit extends from a peripheral edge of the drape to the fenestration between the right and left panels. Right and left flaps extend from the right and left panels and overlap each other and cover the slit. A fluid control pouch surrounds at least part of the fenestration. The surgical drape can be used on either the right or left shoulder of the patient and covers the entire patient. The present invention also pertains to a method of draping a patient with the surgical drape.

28 Claims, 4 Drawing Sheets

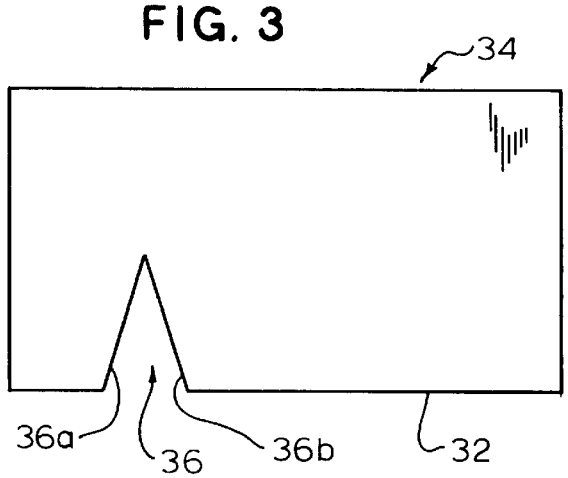
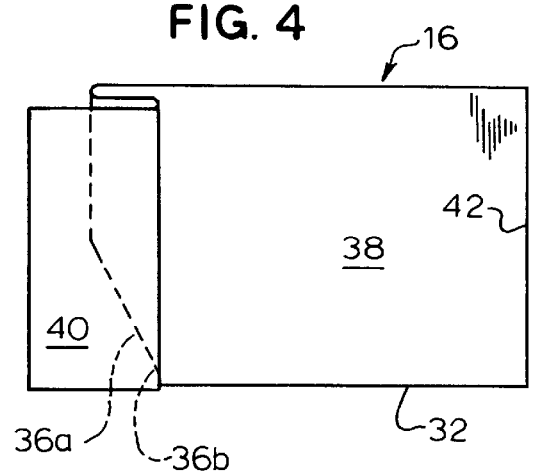
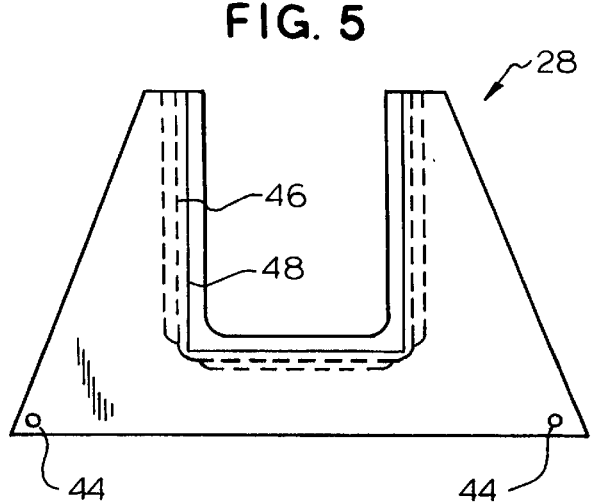
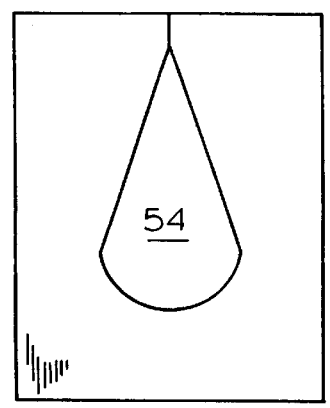
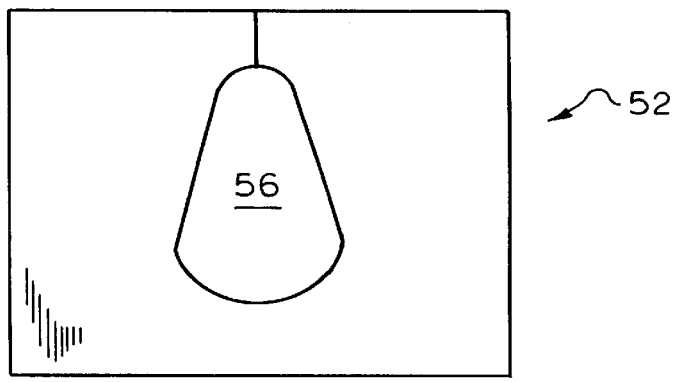

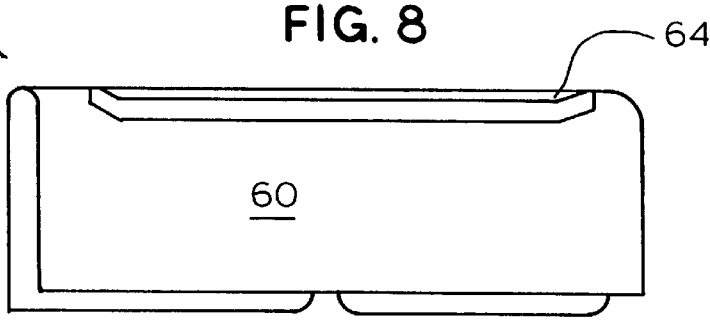
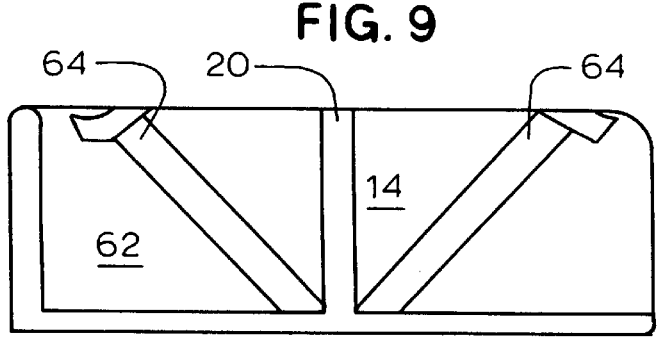
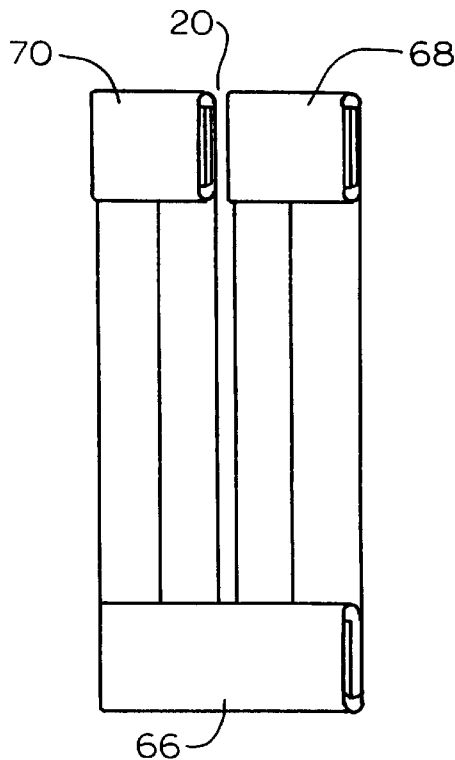
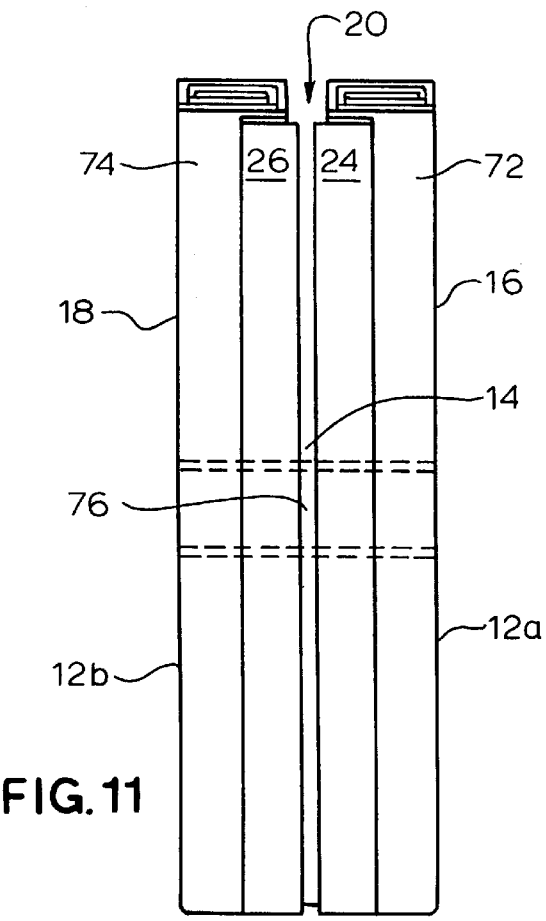

SURGICAL SHOULDER DRAPE

FIELD OF THE INVENTION

The present invention generally relates to surgical drapes, and more particularly to surgical drapes used for shoulder surgery when the patient is in the beach chair position.

BACKGROUND OF THE INVENTION

Surgical drapes are commonly used in the medical industry during surgical procedures. Surgical drapes serve many purposes including isolating the surgical area, protecting the patient and protecting the sterile field. Surgical drapes used in the medical industry are constantly undergoing redevelopment. One reason for redevelopment of surgical drapes is that surgical procedures change; although, there are many reasons for improving surgical drapes.

One change in surgical procedures has occurred in the procedure for performing shoulder surgery. In the past, shoulder surgery was typically performed with the patient in the so called "lateral position." In the lateral position the patient is positioned lying down laterally on the surgical table. A new patient position for shoulder surgery has been developed. The new position is the so called "beach chair" or Fowlers position. In the beach chair position the patient is seated upright and somewhat reclined, which results in a position similar to a position of a person sitting in a beach chair.

A two-piece lateral surgical drape has been used during shoulder surgery when the patient is in the lateral position. An example of the two-piece lateral drape is shown in FIG. 1. The patient lying laterally on the surgical table is draped for surgery with the two-piece drape by separately placing one section and then the other section on the patient. Each section has a cut-out for placing the drape around the shoulder. Prior to the present invention, however, there has not been a drape designed for medical procedures when the patient is in the beach chair position for a shoulder procedure.

SUMMARY OF THE INVENTION

The present invention provides a unique drape for use with medical procedures, particularly a surgical drape for use during shoulder surgery when the patient is in the beach chair position. The surgical drape can be used on a patient in the beach chair position for orthopedic surgery, for example. The surgical drape is a one-piece design which covers the entire patient and is universal in that it can be used for surgery on either the left or right shoulder.

The surgical drape effectively provides proper draping of the patient when the patient is in the beach chair position by covering the entire patient, isolating the surgical area and draping the sterile field. The surgical drape has been found to exhibit improved fluid control properties because of its unique design. Also, the surgical drape protects the patient from contact with surgical fluids, in part, by its one-piece design.

The surgical drape has a base panel defining a fenestration and is flexible such that the fenestration can be sealed to the patient and expose any desired area of the shoulder for surgery. Opposing right and left panels extend from the base panel away from the fenestration and a slit extends from a peripheral edge of the drape to the fenestration between the right and left panels. The slit provides access to the fenestration. Right and left flaps extend from the right and left panels, respectively, in an overlapping relationship. The right and left flaps also cover the slit. A fluid control pouch is attached to the base panel and surrounds at least part of the fenestration. The surgical drape may include various areas which have an adhesive, such as adhesive tape, for attaching the areas to desired locations on the drape.

The present invention also pertains to a unique method of draping a patient in the beach chair position. The method of draping a patient includes unfolding the drape from a folded, compact envelope. The envelope is positioned under the axilla (arm pit) and against the patient. The fenestration is sealed to the patient around the shoulder surgical site by adhesive tape. The surgical drape is unfolded both below and above the axilla into elongated folded sections on the right and left side of the axilla. The elongated right and left sides are unfolded to cover the entire patient from head to feet. A top section of the surgical drape above the shoulder can be attached to upstanding poles to create an anesthesia shield. The right and left flaps are positioned around the upper part of the patient as desired to completely cover the patient. The fluid control pouch is shaped by adjusting the position of a drawstring until the desired position of the pouch is achieved. A suitable drawstring useable with the surgical drape is disclosed in U.S. Pat. No. 5,002,069. The patient which is in the beach chair position is now fully draped with the unique surgical drape for the medical procedure on the shoulder.

BRIEF DESCRIPTION OF THE DRAWINGS

FIG. 3 is a layout of the material used to make a right panel of the drape shown in FIG. 2.

FIG. 4 is a plan view of the right panel of the drape shown in FIG. 2.

FIG. 5 is a plan view of a fluid control pouch of the drape shown in FIG. 2.

FIG. 6 is a plan view of a film panel for use with the surgical drape of FIG. 2.

FIG. 7 is a plan view of a reinforcement panel for use with the surgical drape of FIG. 2.

FIG. 8 is a plan view of the surgical drape of FIG. 2 folded into an envelope with a patient side showing.

FIG. 9 is a plan view of the envelope of FIG. 8 showing a medical procedure side of the envelope.

FIG. 10 is a plan view of the surgical drape of FIG. 8 partially unfolded.

FIG. 11 is a plan view of the surgical drape of FIG. 10 unfolded further.

DETAILED DESCRIPTION OF PREFERRED EMBODIMENTS

Although the present invention can be made in many different forms, the preferred embodiments are described in this disclosure and shown in the attached drawings. This disclosure exemplifies the principles of the present invention and does not limit the broad aspects of the invention only to the illustrated embodiments.

Figure 1:
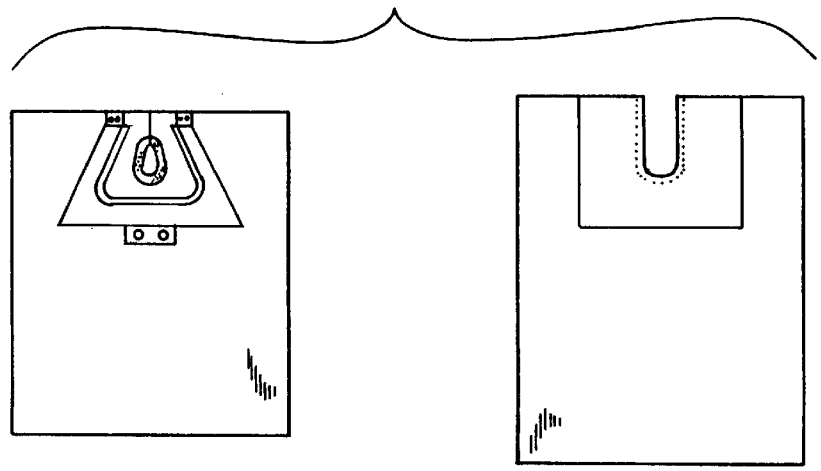
FIG. 1 is a plan view of the existing two-piece drape used for shoulder surgery when the patient is in the lateral position.
Figure 2:
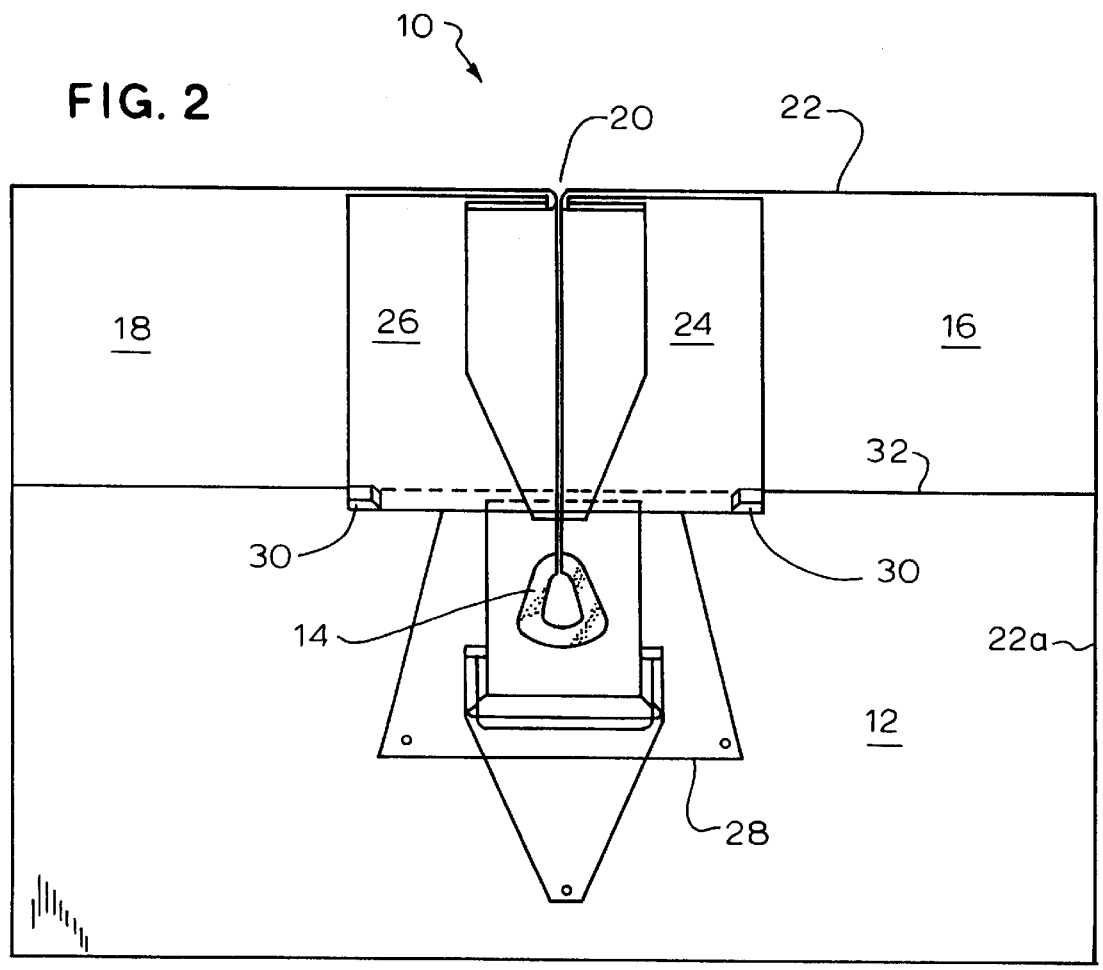
FIG. 2 is a plan view of a drape of the present invention.

A surgical drape 10 made in accordance with the principles of the present invention is shown in FIG. 2. The surgical drape 10 has a base panel 12 defining a fenestration 14. The surgical drape 10 is flexible such that the fenestration 14 can be sealed to the patient and expose any desired area of the shoulder for surgery. Opposing right and left panels 16, 18 extend from the base panel away from the fenestration 14. A slit 20 extends from a peripheral edge 22 of the drape 10 to the fenestration 14. The slit 20 provides access to the fenestration 14. A right flap 24 extends from the right panel 16 toward the left panel 18 and a left flap 26 extends from the left panel 18 towards the right panel 16. The right and left flaps 24, 26 are shown folded back upon themselves in FIG. 2. A fluid control pouch 28 is attached to the base panel 12 and surrounds at least part of the fenestration 14.

The base panel 12 shown in FIG. 2 has a generally rectangular shape in which the fenestration 14 is positioned generally at a mid-area of the base panel 12. The slit 20 extends from an elongated section of the peripheral edge 22 of the rectangularly shaped base panel 12 to the fenestration 14.

The surgical drape 10 may include various areas which have an adhesive for attaching the areas to a desired location. For example, adhesive tape 30 may be provided at corners of the right and left flaps 24, 26. The adhesive tape 30 has a cover or liner that is removed to expose the adhesive and the flap can then be adhered to another part of the surgical drape 10, the patient or any other desired location. Preferably, adhesive tape is also placed around the fenestration so the surgical drape 10 can be sealed to the patient around the surgical site when the patient's shoulder extends through the fenestration 14. Adhesive tape or other appropriate adhesive can be applied to any other areas on the surgical drape 10 where it is desired.

The base panel 12, the right and left panels 16, 18 and the right and left flaps 24, 26 are all constructed from a material suitable for use with surgical drapes. These components of the surgical drape 10 are preferably made from the same type of material, for example, any suitable non-woven material. One material useable with the surgical drape 10 is an Optima® material which is marketed by DuPont. Materials suitable for use with the surgical drape preferably are strong, breathable, drapeable, fluid resistant and low lint.

The right panel 16 is shown in FIG. 2 as a being made from a separate piece of material than the base panel 12. The right panel 16 extends from the base panel 12 by being secured to the base panel 12 along an edge 32. The base panel 12 and right panel 16 can be secured together by glue and preferably the glued edge 32 is sealed such that fluid does not leak through between the base panel 12 and the right panel 16. The right panel 16 is secured to the base panel 12 only along a portion of the edge 32, particularly, from a right outside edge 22a of the surgical drape 10 to the slit 20. The remaining portion of the right panel 16 which is not secured to the base panel 12 forms the right flap 24. The right panel 16 having the right flap 24 can also be referred to as a right flap panel. The right panel 16 and the base panel 12 can be secured together by any other method which produces an acceptable connection for surgical drapes. The right panel 16 may alternatively be formed from the same piece of material which forms the base panel 12. In such a construction, attaching the two panels together would not be necessary. The left panel 18 is similar to the right panel 16 and is a mirror image of the right panel 16. Accordingly, the left panel 18 extends from the base panel 12 on an opposed side of the base panel 12 from the right panel 16.

The slit 20 defines a centerline through the surgical drape 10 dividing the drape into right and left symmetrical halves which are mirror images of each other. The surgical drape 10 can be used on either the right or left shoulder of the patient because the right and left haves are mirror images. In this manner, the surgical drape 10 is universal for beach chair shoulder surgery in that it can be used for either the left or right shoulder without modifying the drape. However, it is contemplated that the inventive surgical drape could be made with right and left halves that are not exact mirror images and still be universally useable on the left and right shoulders. For example, preferably, both the right and left panels 16, 18 have a flap (shown in FIG. 2 as the right and left flaps 24, 26). However, only one of the right or left panels 16, 18 may include a flap which overlaps and closes the slit 20.

The size of the surgical drape 10 is predetermined such that the surgical drape 10 fully covers the patient when in use. The surgical drape 10 fully covers the patient regardless of whether the surgical drape 10 is applied to the right or left shoulder. The size of the surgical drape 10 is selected such that a portion of the drape above the surgical site can be used as an anesthesia shield by clipping the drape to poles. Another portion of the surgical drape 10 below the surgical site is sufficiently long to drape the sterile field when the patient is in the beach chair position. In other words, the surgical drape 10 extends sufficiently close to the floor in the operating room even though the patient is positioned relatively high due to the beach chair position.

The right panel 16 is shown in greater detail in FIGS. 3 and 4. FIG. 3 shows a layout of the material 34 used to make the right panel 16. The layout of material 34 is generally rectangular in shape and includes a cut-out 36. The cut-out 36 is preferably V-shaped and has two edges 36a, 36b which converge at a point. Referring to FIG. 4, the layout of material 34 is folded back upon itself to align the edges 36a, 36b of the V-shaped cut-out 36 and the edges 36a, 36b are secured together, for example by glue. The right panel 16 thus has a connection portion 38 and an adjustment portion 40 extending from the connection portion 38. The connection portion 38 is secured to the base panel 12 along the edge 32 from an edge 42 to the secured together cut-out edges 36a, 36b. The adjustment portion 40 is not secured to the base panel 12. The adjustment portion 40 extends at an angle from the connection portion 38 because of the cut-out 36. The angled adjustment portion 40 provides the surgical drape 10 with flexibility when draping a patient to adjust the location of the drape, particularly the flap, as desired relative to the surgical field. The flexible adjustment of the adjustment portion 40 provides for a better custom fit of the surgical drape 10 on the patient in the beach chair position. The left panel 18 is similarly constructed as the right panel 16.

Referring to FIG. 2, the right flap 24 can be unfolded toward the left panel 18 such that the right flap 24 overlaps the left panel 18 and the slit 20. Likewise, the left flap 26 can be unfolded toward the right flap 24 such that the left flap 26 overlaps the right panel 16 and the slit 20. When a patient is draped for a shoulder medical procedure, the surgical drape 10 is placed on the patient by using the access slit 20 to pass the drape by either the right or left shoulder until the shoulder reaches the fenestration 14. The right and left flaps 24, 26 are unfolded to overlap portions of the surgical drape 10 and to cover the slit 20. In this manner, the shoulder of a patient can be isolated for a medical procedure. The draping procedure is more fully described below.

The fluid control pouch 28 which is secured to the base panel 12 is shown in FIG. 5. The pouch 28 is a known pouch, but has not previously been used on a surgical drape for shoulder medical procedures when the patient is in the beach chair position. The pouch 28 is generally U-shaped and surrounds a substantial portion of the fenestration. The pouch 28 can be sealed to the base panel 12 by any acceptable method for making surgical drapes, such as by double faced tape. The pouch 28 includes two drainage ports 44 which are closed prior to use. The drainage ports 28 are opened to define fluid flow paths from inside the pouch to outside the pouch and drain surgical fluids collected in the pouch during the medical procedure. The drainage ports 28 are beveled to reduce or prevent clogging by surgical debris. A drawstring 46 is provided at a pouch edge 48 which is spaced away from the base panel 12. The drawstring 46 is formed from a malleable and form retentive material such that the pouch can be held up and out and shaped as needed to enhance fluid collection.

The surgical drape 10 may also include a film panel 50 and a reinforcement panel 52 shown in FIGS. 6 and 7. The film panel 50 has an opening 54 which corresponds to the fenestration 14 and preferably has a smaller size than the fenestration 14. The film panel is sealingly secured, e.g. laminated, to the base panel 12 around the fenestration 14 with the opening 54 aligned with the fenestration 14. The film panel 50 provides increased strength in the fenestration area which may be needed during surgery and for securing the pouch 28 to the base panel 12. The film panel 50 can in a polyethylene film, for example. The smaller size of the opening 54 in the film panel 50 results in a portion of the film panel 50 being exposed in the fenestration 14 as can been seen in FIG. 2. The exposed portion of the film panel 50 provides a surface which can be effectively sealed to the patient to prevent fluids from leaking past the surgical site. Double sided adhesive tape can be applied to the exposed area of the film panel to sealingly secure the surgical drape 10 to the patient.

Referring to FIG. 7, the reinforcement panel 52 has an opening 56 which corresponds to the fenestration 14 and is approximately the same size as the fenestration 14. The reinforcement panel 52 is sealingly secured, e.g. laminated, to the base panel 12 over the film panel 50 and around the fenestration 14 with the opening 56 aligned with the fenestration 14. The reinforcement panel 52 is made from the same material as the base panel 12 and also provides increased strength in the fenestration area. The reinforcement panel 52 and the film panel 50 assist in directing surgical fluids to the pouch 28 in the high fluid contact area of the fenestration 14. The pouch 28 is attached to the base panel 12 between the film panel 50 and the reinforcement panel 52.

Application of the surgical drape 10 to a patient will now be described when the patient is in the beach chair position. Referring to FIGS. 8 and 9, the surgical drape 10 is in a folded, compact envelope 58 form with a patient side 60 and a procedure side 62 having the fenestration 14 and the slit 20 exposed. The surgical drape 10 may have labels placed at various locations on the drape which provide certain instructions. For example, the patient side 60 of the envelope 58 may have a label which states "PLACE UNDER AXILLA" as an instruction to place the patient side 60 against the patient and under the axilla (arm pit). Various arrows with labels "FOLD" may be included to provide instructions on unfolding the surgical drape 10 to drape a patient.

All adhesive liners 64 covering the adhesive tape around the fenestration 14 are removed to expose the fenestration tape. The envelope 58 is positioned under the axilla with the patient side 60 against the patient. The fenestration 14, particularly the adhesive tape on the film panel 50, is adhered to the patient around the shoulder surgical site to create a seal around the shoulder.

Referring to FIG. 10, the portion of the folded surgical drape 10 below the axilla is a folded base panel 66. The folded base panel 66 is unfolded downward and allowed to fall towards the floor. This folded portion of the surgical drape 10 is the base panel 12. A folded right panel 68 and a folded left panel 70 are unfolded upwards past the patient's head without crossing the folded panels 68, 70. The folded right and left panels 68, 70 are the right and left panels 16, 18, respectively.

The folded right and left panels 68, 70 are unfolded into elongated, folded right and left sides 72, 74 as shown in FIG. 11. The folded right side 72 includes a right side 12a of the base panel 12, the right panel 16 and the right flap 24. Similarly, the folded left side 74 includes a left side 12b of the base panel 12, the left panel 18 and the left flap 26. A fenestration shield 76 may be included to protect the fenestration during shipping and handling and is removed during draping of the patient. The fenestration shield can be made from tissue paper.

Figure 12:
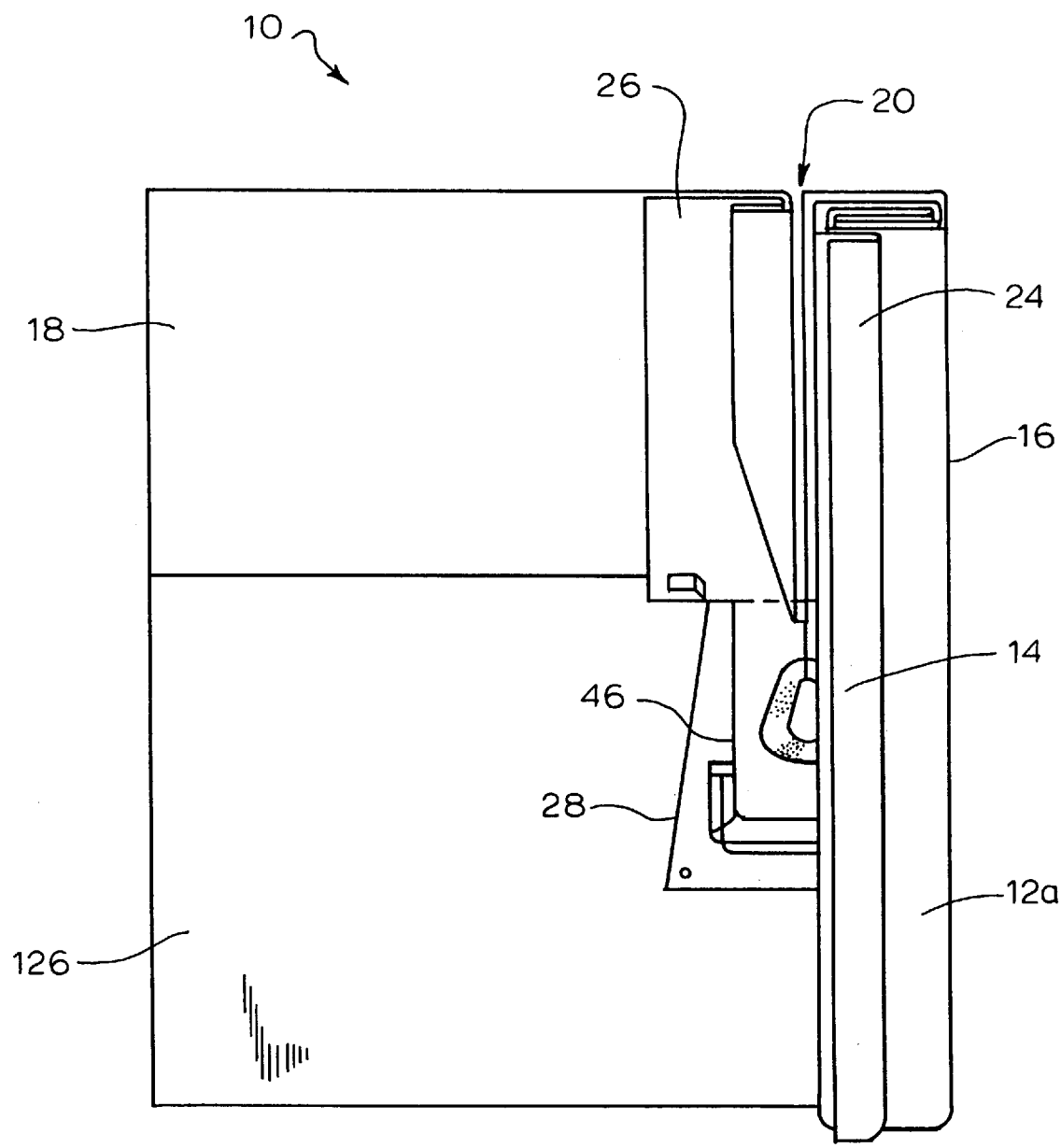
FIG. 12 is a plan view of the surgical drape of FIG. 11 further unfolded.

The folded right and left sides 12a, 12b of the base panel 12 are unfolded to cover the entire area of the patient below the shoulder. FIG. 12 shows the left side of the drape 10 being unfolded, while the right side is similarly unfolded. The right and left panels 16, 18 are unfolded to cover the area of the patient above the shoulder. A top section of the surgical drape 10 above the shoulder can be attached to upstanding poles to create an anesthesia shield. This top section can include the right and left panels 16, 18. The right and left flaps 24, 26 are unfolded and draped around the patient, particularly the patient's head, as desired. The right and left flaps 24, 26 extend from the right and left panels 16, 18 at angles which permits easy adjusting and positioning of the flaps. The right and left flaps 24, 26 can be adhered to the drape by removing liners covering adhesive tape on the flaps.

The fluid control pouch 28 is shaped by adjusting the position of the drawstring 46 until the desired position of the pouch 28 is achieved. The patient which is in the beach chair position is now fully draped for the medical procedure on the shoulder. The above procedure for draping the patient is the same whether the patient is being draped for a medical procedure on the right or left shoulder. Also, additional drapes are not necessary because of the design of the drape for the beach chair position. However, additional drapes, such as a standard U-shaped drape, can be used in conjunction with the present invention.

While the preferred embodiments have been illustrated and described, numerous changes and modifications can be made without significantly departing from the spirit and scope of this invention. Therefore, the inventors intend that such changes and modifications are covered by the appended claims.

We claim as our invention:

1. A surgical drape comprising:

a base panel defining a fenestration;

a pouch attached to the base panel and surrounding at least part of the fenestration;

a first panel extending from the base panel in a first direction away from the fenestration;

a second panel extending from the base panel away from the fenestration in the first direction, the first and second panels being positioned opposed to each other, and forming an access extending from an edge of the surgical drape to the fenestration and between the first and second panels; and a flap panel extending from one of the first and second panels toward the other of the first and second panels and overlapping the access to the fenestration and the other of the first and second panels.

2. The surgical drape of claim 1 wherein the flap panel is a first flap panel extending from the first panel toward the second panel and overlapping the access to the fenestration, and the surgical drape further comprising a second flap panel extending from the second panel toward the first panel and overlapping the access to the fenestration.

3. The surgical drape of claim 2 further comprising first and second connection portions respectively extending from the first and second flap panels, and first and second adjustment portions respectively extending at angles from said first and second connection portions.

4. The surgical drape of claim 3 wherein each of the adjustment portions is formed by a notch defined in the respective first and second flap panel, wherein the notch has two notch edges which are secured together.

5. The surgical drape of claim 2 wherein the first and second flap panels have an adhesive area capable of securing the first and second flap panels to separate locations on the surgical drape.

6. The surgical drape of claim 1 wherein the flap panel has an adhesive area capable of securing the flap panel to a desired location on the surgical drape.

7. The surgical drape of claim 1 wherein the fenestration is positioned in generally a mid-area of the surgical drape.

8. The surgical drape of claim 7 wherein the surgical drape has a generally rectangular shape.

9. The surgical drape of claim 1 wherein the access to the fenestration extends from an elongated peripheral edge of the surgical drape to the fenestration.

10. The surgical drape of claim 1 further comprising an adhesive area surrounding the fenestration and capable of sealing the surgical drape to a patient around a surgical site.

11. The surgical drape of claim 1 wherein the first panel is constructed from a separate piece of material from the base panel and is sealingly secured to the base panel such that the first panel extends from the base panel.

12. The surgical drape of claim 11 wherein the second panel is constructed from another separate piece of material and is sealingly secured to the base panel such that the second panel extends from the base panel.

13. The surgical drape of claim 1 wherein the flap panel has a connection portion extending from the one of the first and second panels and an adjustment portion extending at an angle from the connection portion.

14. The surgical drape of claim 13 wherein the adjustment portion is formed by a notch defined in the flap panel, wherein the notch has two notch edges which are secured together.

15. The surgical drape of claim 14 wherein the notch is V-shaped.

16. The surgical drape of claim 1 wherein the surgical drape is symmetrical about a centerline defined by the access to the fenestration.

17. The surgical drape of claim 1 wherein the surgical drape is adapted to be placed around either one of a patient's right or left shoulders when the patient is in the beach chair position for shoulder surgery.

18. The surgical drape of claim 1 further comprising:
a film panel laminated to the base panel and defining a film panel opening aligned with the fenestration; and
a reinforcement panel laminated to the base panel and defining a reinforcement opening aligned with the fenestration, wherein the film panel and the reinforcement panel surround the fenestration.

19. The surgical drape of claim 1 wherein the pouch is generally U-shaped and surrounds a substantial portion of the fenestration.

20. The surgical drape of claim 19 wherein the pouch has at least one drainage port which defines a fluid flow path from inside the pouch to outside the pouch.

21. The surgical drape of claim 19 wherein the pouch has a drawstring at a pouch edge which is spaced away from the base panel, the drawstring being formed from a malleable and form retentive material.

22. The surgical drape of claim 1 wherein the surgical drape is constructed from a breathable and fluid resistant material.

23. A drape for use during a shoulder medical procedure when a patient is in the beach chair position, the drape comprising:
a panel having a peripheral edge and defining a fenestration in generally a center area of the panel;
a fluid control pouch attached to the panel and surrounding at least part of the fenestration;
a slit in the panel extending from the peripheral edge to the fenestration; and
a flap extending from one portion of the panel and overlapping another portion of the panel wherein the flap covers the slit.

24. The drape of claim 23 wherein the flap is a first flap extending from a first portion of the panel and overlapping a second portion of the panel, wherein the drape further comprises a second flap extending from the second portion of the panel and overlapping the first portion of the panel and covering the slit.

25. The drape of claim 23 wherein the drape is adapted to be placed around either one of a patient's right or left shoulders when the patient is in the beach chair position for the shoulder medical procedure.

26. A method of draping a patient for a shoulder medical procedure when the patient is in the beach chair position with a drape which has been folded comprising the steps of:
placing the folded drape under the axilla of a patient;
placing a patient side of the folded drape against the patient;
securing a fenestration of the drape around a shoulder of the patient;
unfolding a portion of the folded drape below the axilla downward into a lower folded section;
unfolding a portion of the folded drape above the axilla upward into an upper folded section;
unfolding the lower folded section into an unfolded lower section and covering a lower area of the patient with the unfolded lower section; and
unfolding the upper folded section into an unfolded upper section and covering an upper area of the patient with the unfolded upper section.

27. The method of claim 26 further comprising the steps of:
unfolding the portion of the folded drape above the axilla into an upper right folded section and an upper left folded section;
unfolding the upper right folded section to the right to cover the upper area of the patient; and
unfolding the upper left folded section to the left to cover the upper area of the patient.

28. The method of claim 27 further comprising the steps of:
unfolding right and left flaps connected to respective upper right and left panels of the drape; and
securing the unfolded right and left flaps to the drape.

* * * * *